United States Patent [19]

Landry et al.

[11] Patent Number: 4,655,949
[45] Date of Patent: Apr. 7, 1987

[54] LUBRICATING OIL COMPOSITIONS CONTAINING ORGANOMETALLIC ADDITIVES

[75] Inventors: James F. Landry, LaHabra; Michael C. Croudace, Huntington Beach; Harry P. On, Jr., LaHabra; Sidney Y. Shen, Hacienda Heights, all of Calif.

[73] Assignee: Union Oil Company of California, Los Angeles, Calif.

[21] Appl. No.: 726,804

[22] Filed: Apr. 24, 1985

[51] Int. Cl.$^4$ ............................................. C16M 133/00
[52] U.S. Cl. ............................... 252/51.5 R; 252/42.7; 252/49.9; 252/46.4
[58] Field of Search ............... 252/42.7, 51.5 R, 49.9, 252/46.4

[56] References Cited

U.S. PATENT DOCUMENTS 4,069,249  1/1978  Gaudette et al. .
4,152,345  5/1979  Gaudette et al. .
4,225,502  9/1980  Gaudette et al. .
4,387,244  6/1983  Scanlon et al. .

OTHER PUBLICATIONS

Bulletin on Hamplex® NPG from the Organic Chemicals Div. of W.R. Grace & Co.

Primary Examiner—William R. Dixon, Jr.
Assistant Examiner—Cynthia A. Prezlock
Attorney, Agent, or Firm—Dean Sandford; Gregory F. Wirzbicki; Robert J. Baran

[57] ABSTRACT

This invention provides novel lubricating oil compositions comprising an organometallic additive, including a metal selected from Groups I, Ib, and VIII of the Periodic System of Elements, e.g. Na, K, Cu, Co, Ni or Fe, chelated with the reaction product of formaldehyde, an amino acid and a phenol, dissolved in a lubricating oil. Depending on the choice of the metal, the above organometallic additive imparts rust inhibition, sludge dispersant, wear reduction and anti-oxidant properties to said lubricating oil compositions.

35 Claims, No Drawings

LUBRICATING OIL COMPOSITIONS CONTAINING ORGANOMETALLIC ADDITIVES

BACKGROUND OF THE INVENTION

1. Field of the Invention

This invention relates to lubricating oil compositions comprising organometallic additives useful to increase the rust inhibition, sludge dispersant, wear reduction and anti-oxidant properties of the lubricating oil.

2. Summary of the Art

Various metal chelating agents are known for solubilizing metals in nonaqueous systems. For example, in U.S. Pat. No. 4,397,244, a class of such chelating agents are disclosed which are synthesized by (1) reacting formaldehyde and an amino acid and (2) then reacting the resulting product, with a phenol. The metal chelating agent may be in the acid form or the alkali metal or ammonium salt thereof. The chelation of Cu(II) and Fe(III) ions with this chelating agent is specifically disclosed and while it is claimed that other metal ions may be chelated therewith, the identity of such other metals is not found in the patent. (It is reported in a trade brochure, published on one of the individual metal chelating agents disclosed in this patent, that nickel and cobalt may be complexed.) The chelation of other metal ions to provide oil-soluble complexes may be found in U.S. Pat. Nos. 4,069,249; 4,152,345 and 4,225,502; however the chelating agents of these patents are structurally different than the chelating agents of U.S. Pat. No. 4,387,244 and it is well known that the degree of chelating ability of chelating agents is not predictable, a priori, from the chemical structure of the chelating agent, alone.

Organometallic additives are many times incorporated into lubricating oils to provide lubricating compositions having special and improved properties. For example certain copper and lead compounds impart corrosion resistance to lubricating oils. Organoboron compounds provide extreme pressure, anti-wear and friction reducing properties. Organozinc compounds are also known wear reducing additives. However, the determination of whether an organometallic compound will "work", that is, will impart the desired properties when added to a lubricating oil is also unpredictable, with a reasonable degree of certainty, from the chemical structure of such organometallic compound alone.

Therefore, it is one object of this invention to provide lubricating oil compositions having improved corrosion and wear properties and stability to oxidation.

Additional objects, advantages and features of the invention will become apparent to those skilled in the art from the following description.

SUMMARY OF THE INVENTION

Lubricating oil compositions comprising an organometallic additive represented by the general formula:

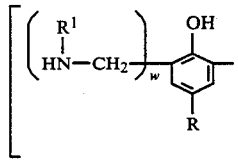

-continued

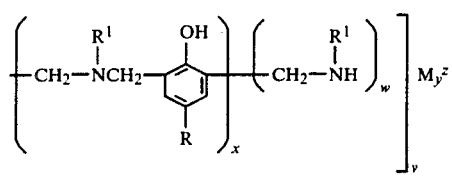

wherein M is selected from the group consisting of members of Groups I, Ib and VIII of the Periodic System of Elements; $R^1$ is selected from the group consisting of radicals represented by the formula

wherein $R^2$ is selected from the group consisting of hydrogen, hydrocarbyl radicals and heteroatom-substituted hydrocarbyl radicals wherein said heteroatoms are selected from the group consisting of halogen, oxygen, sulfur, nitrogen and phosphorus atoms, $R_3$ is selected from the group consisting of hydrogen and lower alkyl radicals; R is selected from the group consisting of hydrocarbyl radicals and hetero atom-substituted derivatives thereof wherein said heteroatoms are selected from the group consisting of halogen, oxygen, sulfur, nitrogen and phosphorus atoms; and v, w, x, y and z are integers; dissolved in a lubricating oil, have, depending on the choice of M, improved sludge dispersant, wear reduction, rust-inhibition and/or anti-oxidant properties.

In the novel compositions, wherein M is a sodium or potassium the lubricating oil composition has unexpectedly improved rust-inhibition properties. When M is sodium copper, cobalt or iron (and especially sodium) the organometallic additive imparts unexpectedly improved dispersant properties to the lubricating oil. Moreover, when the M is selected from the group consisting of cobalt, sodium, copper and potassium the organometallic additive imparts unexpectedly improved wear reduction properties to the lubricating oil compositions. Finally, when M is selected from the group consisting of sodium, cobalt and copper an organometallic additive is obtained which imparts unexpectedly improved oxidative stability when dissolved in a lubricating oil.

DETAILED DESCRIPTION OF THE INVENTION

In the above organometallic additives used to provide the lubricating oil compositions of this invention, x is an integer which represents the degree of polymerization or oligimerization of the organic reactants that are combined to provide the organo chelating moiety of the organometallic additive, i.e. the organo chelating moiety is represented by that portion within the outer brackets of the above general formula. Preferably x ranges from 0 to about 25, more preferably from about 1 to about 15, e.g. 2 to about 6. y represents the number of metal ions chelated by the organo chelating moiety of the above organometallic additive and preferably ranges from 1 to about 30, more preferably from about 1 to about 10, e.g. from 1 to 5. z represents the valence of M and ranges from 1 to 6, preferably from 1 to 3, e.g. 2. w is an integer of 0 or 1, but at least one w must be 1 if x is 0. v represents the number of organo chelating moieties coordinated with a single M and varies from 1 to 6, preferably from 1 to 3, e.g. 1 or 2. In general, the product of y and z will approach the value of the product of x and v, i.e. the organo chelating moiety of the organometallic additive is utilized to its maximum chelating ability, but the product of y and z may be much lower than the product of x and v and still provide compositions having the desired properties as lubricating oil additives.

In the above composition M is preferably selected from metal ions of the group consisting of Na, K, Cu, Co, Ni and Fe. The individual metal ion may be selected on the basis of the desired end use properties for the organometallic additive. For example, as noted above, if the organometallic additive is to be utilized to provide sludge dispersant properties to the lubricating oil, M is preferably Na, and so forth.

In the above composition R is preferably selected from the group consisting of hydrocarbyl radicals having from 1 to 1000 carbon atoms, more preferably from 3 to 75 carbon atoms, and most preferably from about 3 to 15 carbon atoms, e.g. 8 or 9 carbon atoms. Thus R may represent a radical selected from the group consisting of n-propyl, isopropyl, n-butyl, isobutyl, n-octyl, n-nonyl, n-dodecyl, 2,3-dimethyl-hexyl, n-octadecyl, 3,3-dimethyltetradecyl, 3-phenyl-2,4-diethylhexyl, etc.

For hydrocarbon solubility, R may be a polyisobutyl, poly-n-butyl or polypropyl radical having a molecular weight of from about 300 to about 14,000. Radicals resulting from the copolymerization of mixtures of $C_2$ to $C_6$ olefins and diolefins, e.g. ethylene, propylene, isobutylene, etc., having a molecular weight of from about 100 to about 15,000 are also suitable for the compositions of this invention.

In the composition of the present invention $R^2$ may be selected from the group consisting of hydrogen, a lower alkylgroup having from 1 to about 6 carbon atoms,

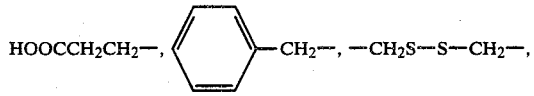

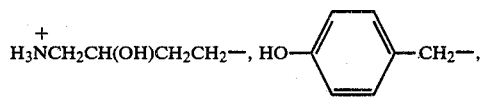

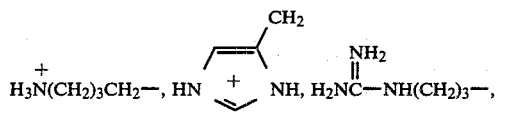

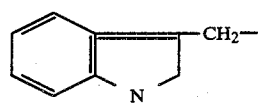

Since the above organometallic additives are dissolved in lubricating oils, R, $R^2$ and, to some extent, $R^3$ are selected to provide the requisite solubility in the lubricating oil of choice. For example, when the lubricating oil is a hydrocarbon the number of carbon atoms in either or both R and $R^2$ will generally be greater than when a polyalkylene glycol lubricating oil is the choice.

It is generally preferred, if hydrocarbon solubility is desired, to increase the number of carbon atoms on the R group rather than the $R^2$ group since bulky $R^2$ groups may interfere with the chelating efficiency of the adjacent carboxyl group.

Any of R, $R^1$, $R^2$ and/or $R^3$ may represent more than one radical since the organo chelating moiety may be prepared by reacting mixtures of amino acids and/or phenols as described below.

The lubricating oil compositions of this invention may be prepared in a three or four step reaction procedure; said number of steps depending on the choice of M. In the first step, formaldehyde is reacted with an amino acid of the general formula $H_2NCR^2R^3COOH$ in a basic aqueous solution. For example, the pH of the solution may be maintained at from about 7.5 to about 8.0 with sodium or potassium hydroxide or other alkali metal base to provide a first product. In the second step, the first product is reacted with a phenolic compound to provide a second product. For example, while continuing to maintain the pH at from about 7.5 to about 8.0, a methanol solution of a phenol of the general formula:

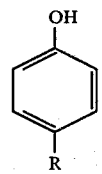

may be slowly added to the first product, and the resulting mixture heated to reflux to thereby provide said second product. Upon cooling and standing, the second product may be separated out as an oily layer while a water and methanol layer is decanted. Said second product is usually obtained as a sodium or potassium salt depending on the basic material utilized in the first step. The second product may be dried and ground to a powder. Vacuum drying is suitable but other types may be employed.

In the third step of the reaction, if a organometallic additive, including a metal other than sodium or potassium is desired, the second product is contacted with the desired metal ion in solution to exchange said metal ion for the sodium or potassium ion and thereby obtain the desired organometallic additive. The contacting may be carried out in a nonaqueous solution, i.e. n-butylether, or any other solvent which will dissolve at least a portion of the second product and a salt of the other metal ion. The efficiency of the reaction between the second product and the metal salt may be conveniently increased by carrying out the contacting under conditions of reflux. A suitable temperature range for effecting the third step of the reaction is from 100° to 200°, preferably from 100° to 145° C. The time for contracting the product of the second step with the other metal ion may range from 1 to 12 hours, preferably from 1 to 4 hours.

The organometallic additive, comprising a metal ion other than sodium or potassium, may be conveniently separated from the nonaqueous solvent by water washing to separate residual metals. The washed mixture is then vacuum distilled to remove excess solvent and the desired organometallic additive recovered.

It will be appreciated from the above reaction scheme that $R^1$ is the residue resulting from the alpha-amino acid and $R^2$ and $R^3$ represent the alpha substituents thereof. For example, if the amino acid used is glycine, $R^2$ and $R^3=H$; if alanine is used, $R^2=CH_3$ and $R^3=H$, etc. $R^3$ is limited to hydrogen and lower alkyl radicals, e.g. $C_1$ to $C_6$ alkyl radicals; however, $R^2$ is not so limited but may also be a hydroxyalkyl, thioalkyl, phenylalkyl, or other organo group. By way of illustration, the following list contains various $R^2$ substituents which are deemed to be within the scope of the present invention, as well as the name of the amino acid from which the substituents is obtained. ($R^3=H$ unless noted otherwise.)

| $R^2 =$ | |
|---|---|
| H— | glycine |
| $CH_3$— | alanine |
| $CH_3CH_2$— | alpha-amino butyric acid ($R^3 = CH_3$) |
| $CH_3CH_2CH_2$— | iso-leucine acid |
| $(CH_3)_2CHCH_2$— | leucine |
| $CH_3CH_2CH(CH_3)$— | 2-amino-3-methyl-pentanoic acid |
| $HO-CH_2$— | serine |
| $CH_3CH(OH)$— | threonine |
| $HSCH_2$— | cysteine |
| $CH_3SCH_2CH_2$— | methionine |
| $H_2NCOCH_2$— | asparagine |
| $H_2NCOCH_2CH_2$— | glutamine |
| $HOOCCH_2$— | aspartic acid |
| $HOOCCH_2CH_2$— | glutamic acid |
| $(CH_3)_2CH$— | valine |
| 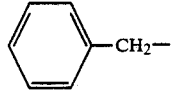 | phenylalanine |
| 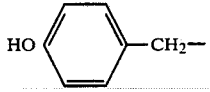 | tyrosine |
| 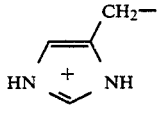 | histidine |
| 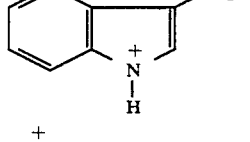 | tryoptophan |
| $\overset{+}{H_3N}(CH_2)_3CH_2$— | lysine |
| $\overset{+}{H_3N}CH(OH)CH_2CH_2$— | hydroxylysine |
| $\underset{\underset{+}{NH_2}}{\overset{\parallel}{H_2NCNH(CH_2)_3}}$— | arginine |

The novel lubricating oil compositions of this invention are prepared by combining a minor amount of the above organometallic additive, of choice, with a major amount of a suitable lubricating oil to provide the novel lubricating compositions. Said novel lubricating compositions have extreme pressure, anti-wear, friction reducing, corrosion inhibition and anti-oxidation properties depending on the selection of M. The organometallic additives are preferably incorporated in the lubricating oil at a concentration ranging from about 0.0001 to about 10 percent, more preferably, from about 0.01 to about 1 percent, e.g. about 0.04 percent, by weight. Said organometallic additives may be used in a wide variety of lubricating oils, for example, mineral oil (preferably automobile engine oil), synthetic oil, industrial oils, for example, cutting oil, metal working fluids and grease. In addition, the organometallic additives may be added to lubricating oils derived from paraffins, naphthenic or mixed base crude petroleum oils, that have been subject to solvent and/or sulfuric-acid treatment, aluminum chloride treatment, hydrogenation and/or other refining treatments.

Preferred distillate lubricating oils which are improved by the addition of the additives herein have an initial boiling point within the range of 350° F. to about 475° F., an end point in the range of about 500° F. to about 1,100° F., and a flash point not lower than 110° F.

Lubricants derived from oil shale are suitable for incorporation of the above organometallic additives therein. Oil shale is generally composed of a variety of compact sedimentary rock, generally laminated, that contains little or no oil but does contain organic material known as kerogen, which is derived from aquatic organisms or waxy spores and pollen grains and which is convertible to oil by heat. Crude shale oil, in combination with water, gas and spent shale containing a carbonaceous residue and mineral matter, is formed by the pyrolysis of oil shale. The hydrocarbons of shale oil are highly unsaturated, resembling the products of thermal cracking of petroleum, as would be expected because of the pyrolytic origin of shale oil. Once the shale oil is extracted, it is subjected to conventional hydrotreating procedures to produce a variety of hydrocarbon products, including lubricating oils.

Synthetic lubricating oils useful herein are those oils derived from a product of chemical synthesis (man-made oils). Typical examples of such compositions include the polyglycol fluids (i.e., polyalkylene glycol); silicones which consist of a silicon-oxygen polymer chain to which are attached hydrocarbon branches composed of either alkyl or phenyl groups; phosphates; polyphenyl esters; synthetic hydrocarbons and various esters of organic acids and alcohols.

The polyalkylene glycol lubricating oils suitable for use herein preferably are derived from the reaction product of the appropriate alkylene oxides. The alkylene moiety of the above lubricating oils have a carbon chain of from about 1 to about 10 carbon atoms. The polyalkylene glycol may preferably comprise from about 200 to about 1,000 carbon atoms, most preferably from about 200 to about 800 carbon atoms. Representative examples of suitable polyalkylene glycols include, polyethylene glycol, polypropylene glycol, polyisopropylene glycol, polybutylene glycol and the like.

Synthetic lubricating oils derived from hydrocarbons are generally of two types, namely dialkylated benezene and polymerized alpha-olefins. Dialkylated benzene herein is formed from the condensation product of the appropriate alkyl compound and has a carbon chain from about 5 to about 50 carbon atoms, preferably from about 8 to about 20 carbon atoms; and a molecular weight of from about 200 to about 1,500, preferably from about 300 to about 700. Representative compounds include di-n-decylbenzene, n-decyl-n-tetradecylbenzene, and n-nonyl-n-dodecylbenzene.

Alpha-olefins suitable for use in preparing lubricating oils herein are characterized by the formula $R^4CH=CH_2$ wherein $R^4$ is a radical selected from the group of hydrogen and alkyl radicals having about 4 to about 18 carbon atoms, preferably from about 6 to about 10 carbon atoms, and having a molecular weight of from about 80 to about 300, preferably from about 100 to about 200. Typical compounds include 1-octene, 1-decene and 1-dodecene.

Phosphates suitable for use herein as synthetic lubricating oils are the phosphate esters having the formula $O=P(OR^5)_3$, wherein $R^5$ is aryl or alkyl having from about 4 to about 20 carbon atoms, preferably from 6 to about 10 carbon atoms, and have a molecular weight within the range of from about 200 to about 1,000, preferably from about 300 to 550. Representative compounds include trioctyl phosphate, tricresyl phosphate and dicresyl methyl phosphate.

Esters of organic acids which are suitable for use herein are synthetic lubricating oils preferably are selected from organic acids having carbon chains of from 4 to 40 carbon atoms. Organic acids which may be reacted with the alcohols herein include caproic, decanoic, sebacic, laurel, oleic, stearic, palmitic, etc. Likewise, alcohols herein may be either natural or synthetic in origin, for example, pentaerythritol, trimethylolpropane, amyl, 2-ethyl-hexanol or lauryl alcohol, may be used to form the desired ester. The esters are formed using conventional methods. For example, the esters may be prepared by reaction of the desired alcohol with the desired acid, acid anhydride or acid halide using conventional reaction conditions and techniques.

If desired, the compositions of the present invention may include other additives commonly used in lubricating oils. Thus, there may be added to the oil compositions of this invention rust inhibitors, emulsifying agents, dyes, haze inhibitors, anti-static agents, detergents, dispersants, viscosity index improvement agents, pour point reducing agents, other extreme pressure additives, corrosion inhibitors and oxidation inhibitors, Soaps or other thickening agents may be added to the lubricating oil compositions to form compositions having the consistency of grease.

The invention is further illustrated by the following examples which are illustrative of a specific mode of practicing the invention and are not intended as limiting the scope of the appended claims.

EXAMPLE 1

This example illustrates the preparation of the organometallic additives used in the lubricating oil compositions of the present invention wherein $R^2=H$ and $R=$nonyl. A mixture of water (64 ml), glycine (15 g) and KOH (4 g) is adjusted to a pH of 8 with 1M HCl. A solution of formaldehyde (36.5 g of 37% formaldehyde in water) and KOH (4 g) is then added to the above mixture over a 40 minute period to provide a reaction mixture. Methanol (600 ml) is added as a cosolvent, to the reaction mixture and the pH is adjusted to 7.5. A mixture of nonylphenol (65.4 g) and methanol (200 ml) is then added over a period of two hours to the cosolvent-containing reaction mixture. During the first ½ hour the cosolvent-containing reaction mixture is heated to 56° C. and held at that temperature throughout the addition. After the addition is complete the temperature of the resulting mixture is elevated to 72°–73° C. and refluxed for 3.5 hours. The mixture is then slowly cooled to room temperature and the phases are allowed to separate. The organic layer is separated and dried leaving a powdery solid (81.4 g). The pure composition is extracted from the solid by acetonitrile to provide a potassium salt.

Cupric acetate (2.0 g, 0.01 mole) and the above potassium salt (10 g, 0.01 mole) are added to 50 ml of n-butyl ether. The mixture is refluxed for 4 hours. Afterwards the mixture is filtered, and the organic solution is washed with water and saturated aqueous sodium chloride solution. After drying over potassium carbonate, rotary evaporation yields 9.0 g of the copper salt.

The zinc, lead, manganese, cobalt and iron salts are made using a similar procedure except that the appropriate metal acetate is substituted for cupric acetate. These salts as well as the sodium salt (made by replacing KOH with NaOH and carrying out the first two steps of the above reaction) are tested as dispersants for lubricating oils in Example II, below.

EXAMPLE II

The organometallic additives prepared as in Example I, are blended into lubricating oil at the concentrations given below and tested in the Cincinnati Millicaron Thermal Stability Test (CMTS Test). The amount of sludge that forms during the test is given in Table I. To carry out the CMTS test, a 250-ml beaker with 100 ml of the lubricating oil composition and solid steel and copper rods are placed in an oven at 135° C. for 168 hours. The CMTS test quantifies oil degradation through viscosity increase, D-664A neutralization number increase, copper rod weight loss/appearance, steel rod weight loss/appearance, and total sludge. In a vast majority of the cases, if the total sludge is below 25 mg, the CMTS specification maximum, the result of the CMTS results meet specification. Thus, only the CMTS sludge result is reported.

TABLE 1

| M = | wt. %[a] | Cincinnati Milacron Sludge, mg/100 ml |
|---|---|---|
| — | — | 20.8 |
| Zinc | 0.04% | 8.4 |
| Lead | 0.04% | 17.7 |
| Sodium | 0.005% | 4.8 |
| Manganese | 0.04% | 5.7 |
| Cobalt | 0.04% | 8.5 |
| Copper | 0.04% | 8.4 |
| Iron | 0.04% | 8.7 |

[a]All lubricating oil compositions contain 0.38 wt. % Ethyl 735 (2,6-di-tert-butylphenol) in 150 neutral base stock.

As can be seen by the above, the sludge is reduced in the lubricating oil compositions of this invention as compared to the lubricating oil not including the above described additive organometallic additives. The sodium additive is especially effective, as a dispersant, as compared to the control.

EXAMPLE III

Certain of the organometallic additives, prepared as in Example I, are tested for enhancing the oxidative stability of a lubricating oil by use of the Penn State Microoxidation Test. In this test a flat bottom glass tube containing a metal disc with a lip is used. A thin film of oil is placed on top of the metal disc. The thickness of the oil film is usually about 0.01 cm for normal operating conditions. To provide isothermal conditions, the glass tube is submerged in a constant temperature bath, which is an electrically heated aluminum block filled with low melting alloy. The test is run at 400° F.

The oil is oxidized for a fixed period of time in this test. After the test, the oxidized sample is cooled and dissolved in tetrahydrofuran (THF). The dissolved sample is analyzed by gel permeation chromatography (GPC) to determine the molecular weight distribution of the sample. The molecular weight distribution of the oxidized oil is a good measure of the degree of thickening.

The compositions of this invention are compared to other additives and the results reported in Table II. The additives are mixed at 0.5, 1.0 and 2.0 weight percent in 150 Neutral base oil. The resulting mixtures are then treated with 100 ppm of iron naphthenate, since iron, which is found in used engine oils, is believed to catalyze polymerization of initially oxidized products in oil. The iron-treated mixtures are heated to 400° F. for 40 minutes and then analyzed by gel permeation chromatography (GPC) for relative amounts of HMWP (products having molecular weight greater than 1000). The lubricating oil compositions of this invention, i.e. the compositions comprising the copper, cobalt, and sodium additives, described above, enhance the oxidative stability of the lubricating oil control. The copper performs at least slightly better than the other additives tested at 0.5 and 1.0 weight percent. It can, also, be readily seen that the sodium additive performs significantly better than the other additives tested at the 2.0 weight percent level.

TABLE II

Relative Amounts of HMWP Formed in 150 Neutral Containing Various Additives After Microoxidation Testing

| Additive Description | Weight Percent of Additive in 150 Neutral Base Stock | | |
|---|---|---|---|
| | 0.5 | 1.0 | 2.0 |
| 1. None | | 6.2 | |
| 2. M = Copper | 1.7 | 1.1 | 2.2 |
| 3. Elco 106, ZnDDP[a] | 8.7 | 2.2 | 1.7 |
| 4. Elco 108, ZnDDP[a] | 2.2 | 2.6 | 2.4 |
| 5. Elco L-28643, ZnDDP[a] | 1.8 | 4.8 | 2.3 |
| 6. Elco L-34132, ZnDDP[a] | 3.7 | 3.6 | 1.2 |
| 7. Lz 894, dispersant[b] | — | — | 5.7 |
| 8. Lz 936, dispersant[c] | 10.7 | — | 7.2 |
| 9. Lz 6575, Zn dispersant[d] | — | 4.9 | 6.7 |
| 10. ECI 644, dispersant[e] | — | — | 3.9 |
| 11. ECI 645, dispersant[e] | — | 7.0 | 5.2 |
| 12. M = Cobalt | — | 4.8 | 1.7 |
| 13. M = Sodium | — | 2.6 | 0.9 |
| 14. M = Magnesium | — | 3.0 | 4.1 |
| 15. M = Manganese | — | 4.9 | 6.7 |

[a]Zinc bis(dialkyldithiophosphates) available from Elco
[b]Polyalkenylsuccinaminade available from the Lubrizol Corporation.
[c]Non-nitrogen-containing dispersant of the polyester-type available from the Lubrizol Corporation
[d]Zinc-containing dispersant available from the Lubrizol Corporation
[e]Polyalkenylsuccinamides available from the Ethyl Petroleum Additives Division of the Ethyl Corporation

EXAMPLE IV

The above organometallic additives are tested for rust-inhibition properties, when utilized in a lubricating oil composition, by ASTM D-665. In this table the additives are referred to as "salts". For example, M=Cu the "Copper Salt". The results are reported in Table III below.

TABLE III

ASTM D-665 PROCEDURE A RUST INHIBITION TEST OF VARIOUS COMPOSITIONS OF THIS INVENTION

| Sample Number | Composition | % | ASTM D-665 A TEST RESULT |
|---|---|---|---|
| | ALUMINUM SALT | | |
| 1 | Aluminum salt | 0.2 | Fail after 24 hours |
| | 150 Neutral | 99.8 | with 2% rust |
| 2 | Aluminum salt | 0.1 | Fail after 24 hours |
| | VL 81[A] | 1.0 | |
| | 150 Neutral | 98.9 | |
| 3 | Aluminum salt | 0.10 | Fail after 24 hours |
| | Ethyl 735 | 0.38 | |
| | 150 Neutral | 99.52 | |
| | BARIUM SALT | | |
| 4. | Barium salt | 0.70 | Pass |
| | Ethyl 735 | 0.38 | |
| | 150 Neutral | 98.92 | |
| 5. | Barium salt | 0.70 | Pass |
| | VL 81 | 1.00 | |
| | 150 Neutral | 98.30 | |
| 6. | Barium salt | 0.20 | Pass |
| | Ethyl 735 | 0.38 | |
| | 150 Neutral | 99.42 | |
| 7. | Barium salt | 0.20 | Pass |
| | VL 81 | 1.00 | |
| | 150 Neutral | 98.80 | |
| 8. | Barium salt | 0.10 | Pass |
| | DCF 200[B] | 5 ppm | |
| | 200 Neutral | 99.9 | |
| 9. | Barium salt | 0.10 | Pass |
| | DCF 200 | 5 ppm | |
| | 100 Neutral | 45.0 | |
| | 200 Neutral | 54.9 | |
| 10. | Barium salt | 0.10 | Pass |
| | DCF 200 | 5 ppm | |
| | 200 Neutral | 51.9 | |
| | 175 Bright Stock | | |
| 11. | Barium salt | 0.10 | Pass |
| | DCF 200 | 5 ppm | |
| | 200 Neutral | 82.9 | |
| | 175 Bright Stock | 12.0 | |
| 12. | Barium salt | 0.04 | Pass |
| | Ethyl 735 | 0.38 | |
| | 150 Neutral | 99.58 | |
| | CALCIUM SALT | | |
| 13. | Calcium salt | 0.70 | Pass |
| | Ethyl 735 | 0.38 | |
| | 100 neutral | 98.92 | |
| 14. | Calcium salt | 0.50 | Pass |
| | Ethyl 735 | 0.38 | |
| | 100 neutral | 99.12 | |
| 15. | Calcium salt | 0.20 | Borderline |
| | VL 81 | 1.00 | Pass (1 spot) |
| | 150 neutral | 99.58 | |
| 16. | Calcium salt | 0.04 | Fail after 24 hours |
| | Ethyl 735 | 0.38 | |
| | 150 neutral | | |
| | COPPER SALT | | |
| 17. | Copper salt | 0.2 | Fail in two hours with |
| | VL 81 | 1.0 | 10% rust |
| | 150 Neutral | | |
| 18. | Copper salt | 0.04 | Fail in one hour |
| | Lz 677A[C] | 0.70 | |
| | 150 Neutral | 99.26 | |
| | IRON SALT | | |
| 19. | Iron salt | 0.2 | Fail in one hour |
| | VL 81 | 1.0 | |
| | 150 Neutral | 98.8 | |
| | LEAD SALT | | |
| 20. | Lead salt | 0.2 | Fail in two hours with |
| | VL 81 | 1.0 | 10% rust |
| | 150 Neutral | 98.8 | |
| | MAGNESIUM SALT | | |
| 21. | Magnesium salt | 0.04 | Fail after 24 hours |
| | Ethyl 735 | 0.38 | |
| | 150 Neutral | 99.68 | |
| 22. | Magnesium salt | 0.04 | Fail after three hours |
| | VL 81 | 1.00 | with 5% rust |

TABLE III-continued

ASTM D-665 PROCEDURE A RUST INHIBITION TEST OF VARIOUS COMPOSITIONS OF THIS INVENTION

| Sample Number | Composition | % | ASTM D-665 A TEST RESULT |
|---|---|---|---|
|  | 150 Neutral | 98.96 |  |
| 23. | Magnesium salt | 0.2 | Pass |
|  | VL 81 | 1.0 |  |
|  | 150 Neutral | 98.8 |  |
| 24. | Magnesium salt | 0.20 | Pass |
|  | Ethyl 735 | 0.38 |  |
|  | 150 Neutral | 99.42 |  |
|  | MANGANESE SALT |  |  |
| 25. | Manganese salt | 0.20 | Fail in 24 hours with |
|  | VL 81 | 1.00 | 4-6 spots |
|  | 150 Neutral | 98.80 |  |
|  | POTASSIUM SALT |  |  |
| 26. | Potassium salt | 0.04 | Pass |
|  | 150 Neutral | 99.96 |  |
| 27. | Potassium salt | 0.1 | Pass |
|  | 150 Neutral | 99.9 |  |
| 28. | Potassium salt | 0.7 | Pass |
|  | 150 Neutral | 99.3 |  |
|  | SODIUM SALT |  |  |
| 29. | Sodium salt | 0.7 | Pass |
|  | Lz 677A | 0.7 |  |
|  | 150 Neutral | 98.6 |  |
| 30. | Sodium salt | 0.2 | Fail at 24 hours |
|  | VL 81 | 1.0 |  |
|  | 150 Neutral | 98.8 |  |
|  | ZINC SALT |  |  |
| 31. | Zinc salt | 0.04 | Fail after four hours |
|  | Ethyl 735 | 0.38 |  |
|  | 150 Neutral | 99.58 |  |
| 32. | Zinc salt | 0.2 | Fail in one hour |
|  | VL 81 | 1.0 |  |
|  | 150 Neutral | 98.8 |  |
| 33. | Zinc salt | 1.0 | Fail in one hour about |
|  | VL 81 | 1.0 | 50% rust |
|  | 150 Neutral | 98.0 |  |
| 34. | 150 Neutral | 100.0% | Fail in less than one hour |
| 35. | Armeen 18D[D] | 2.0 | Fail in less than |
|  | 150 Neutral | 98.0 | one hour |
| 36. | Ethyl 735 | 0.38 | Fail in less than |
|  | 150 Neutral | 99.62 | one hour |
| 37. | VL 81 | 1.0 | Fail in less than |
|  | 150 Neutral | 99.0 | one hour |

[A]Diphenylamine antioxidant
[B]A silicone anti-foamant
[C]Zinc bis(dialkayldithiophosphate)
[D]Primary amine rust inhibitor These results show that the sodium and potassium additive-containing lubricating oil compositions are effective in preventing rust in the ASTM D665 Procedure A; the potassium additive-containing composition being especially effective in rust-inhibition.

EXAMPLE V

Certain of the above organometallic additives are evaluated for increasing the anti-wear properties of lubricating oils by means of the Four-Ball Wear Test. The lubricating oil compositions tested comprise 1 percent, by weight, of the organometallic additives prepared according to Example 1, in 150 Neutral oil. The results, as may be seen from Table IV, below, indicate that the lubricating oil compositions of the instant invention, i.e. those containing the above described cobalt, sodium, copper, and potassium additives, and, in particular, the lubricating oil composition comprising the cobalt additive, are especially effective in improving the anti-wear properties of the lubricating oil. (Again the additive is referred to as a salt.)

TABLE IV

| | Four-Ball Wear Test[a] | | |
|---|---|---|---|
| Additive | Treat Rate of Additive in Oil wt % | Ball Scar Diameter mm | Average Scar mm$^2$ |
| 1. None (150 Neutral) | — | 0.77 | 0.60 |
| 2. Elco 106 | 1.0 | 0.38 | 0.14 |
| 3. Elco 108 | 1.0 | 0.40 | 0.16 |
| 4. Cobalt salt | 0.5 | 0.55 | 0.30 |
| 5. Cobalt salt | 1.0 | 0.33 | 0.11 |
| 6. Cobalt salt | 2.0 | 0.32 | 0.11 |
| 7. Sodium salt | 1.0 | 0.51 | 0.27 |
| 8. Manganese salt | 1.0 | 0.52 | 0.29 |
| 9. Copper salt | 1.0 | 0.60 | 0.36 |
| 10. Zinc salt | 1.0 | 0.71 | 0.48 |
| 11. Magnesium salt | 1.0 | 0.53 | 0.28 |
| 12. Calcium salt | 1.0 | 0.50 | 0.26 |
| 13. Potassium salt[b] | 1.0 | 0.49 | 0.26 |

[a]Test Conditions: Speed 600 rpm; Load 40 kg; Test time, 1 hour; Test temperature 167° F.
[b]Made according to the procedure of Example 1 by substituting aspartic acid for glycine. ($R^2$ = HOOCCH$_2$—).

EXAMPLE VI

Various novel organo metallic compositions are prepared and the amount of chelated metal is determined. A disodium salt of chelating moiety having the above general formula wherein R is nonyl, $R^2$ and $R^3$ are hydrogen, x is 2 and w is 0 is contacted with the appropriate metal acetate in a toluene solution under reaction conditions. The resulting acetic acid is azeotropically distilled from the reaction mixture to obtain the novel organometallic composition. The yield and percent metal of each organometallic composition is reported in Table V below. Note that the cobalt additive contains slightly more than the predicted metal content.

TABLE V

| Amount of Chelating Moiety g (mole) | Type of Metal Acetate | Amount of Acetate g (mole) | Amount of Toluene, ml | Yield g (moles) | Yield % | % Metal Product results/predict. |
|---|---|---|---|---|---|---|
| 10 (0.0116) | cobalt acetate | 2.90 (0.0116) | 250 | 9.64 (0.105) | 91 | 6.49/6.42 |
| 10 (0.0116) | cupric acetate | 2.12 (0.0116) | 250 | 10.32 (0.0112) | 97 | 5.77/6.89 |
| 10 (0.0116) | zinc acetate | 2.56 (0.0116) | 250 | 9.46 (0.0103) | 89 | 6.55/7.08 |
| 10 (0.0116) | lead acetate | 4.42 (0.0116) | 250 | 10.89 (0.0102) | 88 | 5.7/19.5 |
| 10 (0.0116) | nickel acetate | 2.90 (0.0116) | 250 | 7.47 (0.0082) | 73 | 0.17/6.40 |
| 10 (0.0116) | manganese acetate | 2.02 (0.0116) | 250 | 8.60 (0.0094) | 82 | 8.22/6.01 |
| 10 (0.0116) | iron acetate | 2.03 (0.0116) | 250 | 9.52 (0.0104) | 90 | 4.84/6.11 |
| 10 | aluminum acetate (basic) | (0.0116) | 250 | — | — | 4.22/7.13 |

TABLE V-continued

| Amount of Chelating Moiety g (mole) | Type of Metal Acetate | Amount of Acetate g (mole) | Amount of Toluene, ml | Yield g (moles) | Yield % | % Metal Product results/predict. |
|---|---|---|---|---|---|---|
| (0.0116) | [Al(OOCCH$_3$)(OH)] | | | | | |

EXAMPLE VII

Two crankcase oil formulations, using the above cobalt additive, are tested in the CRC L-38 engine test to measure the corrosion of copper and/or lead bearings. Oils C and D, which include the cobalt additive, are based on a propriety Detergent/Inhibitor package of Exxon Chemical Co. designated as ECA 9194X. The engine test is described at page 21, of the *Handbook of Lubrication*, Vol. I, edited by Booser, 2nd. Printing, CRC Press, Inc. The results are reported in Table VI, below. The formulation designated as C was significantly better than D. It is noted that the CRC L-38 engine test clearly demonstrates that the cobalt additive is not substantially corrosive to copper and/or lead bearings.

TABLE VI

| | A wt. % | B wt. % | C wt. % | D wt. % | E wt. % | Description |
|---|---|---|---|---|---|---|
| Additives | | | | | | |
| ECA 9194X | 7.34 | 7.32 | 7.29 | 6.80 | 6.80 | |
| Cobalt Additive | — | — | 1.13 | 1.00 | — | |
| Amoco 158 | — | — | — | 0.15 | 0.15 | Copper corrosion inhibitor from Amoco Chemical Co. |
| Vanlube SL | — | 0.58 | 0.58 | 0.20 | 0.20 | Anti-oxidant and anti-wear |
| Vanlube AZ | — | — | — | 0.20 | 0.20 | additives Vanderbilt |
| Vanlube 7723 | — | 0.60 | 0.60 | 0.50 | 0.50 | Chemical Co. |
| Paratone 716 | 8.63 | 9.35 | 9.39 | — | — | Viscosity Index Improver from Exxon Chemical (olefin copolymer) |
| Acryloid 772 | — | — | — | 6.00 | 6.00 | Viscosity Index Improver from Rohm & Hass Co. (Methyl methacrylate copolymer) |
| Base Oil Ration | | | | | | |
| 90 | 25 | 24 | 24 | — | | |
| 150 Neutral | 75 | 76 | 76 | — | | |
| 100/110 Neutral | — | — | — | 45 | 45 | |
| 180 Neutral | — | — | — | 45 | 45 | |
| Engine Test Results: | | | | | | |
| Bearing Weight Loss, mg. | 1900 | 270 | 200 | 79 | 39.5 | |

While particular embodiments of the invention have been described, it will be understood, of course, that the invention is not limited thereto since many obvious modifications can be made, and it is intended to include within this invention any such modifications as will fall within the scope of the appended claims.

I claim:

1. A lubricating oil composition comprising an organometallic additive represented by the general formula:

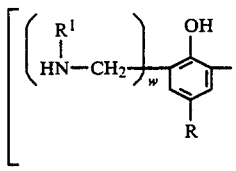

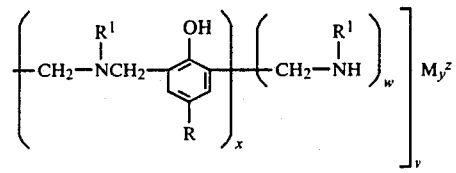

wherein M is selected from the group consisting of members of Groups I, Ib and VIII of the Periodic System of Elements; R$^1$ is selected from the group consisting of radicals represented by the formula

wherein R$^2$ is selected from the group consisting of hydrogen, hydrocarbyl radicals and heteroatom-substituted hydrocarbyl radicals wherein said heteroatoms are selected from the group consisting of halogen, oxygen, sulfur, nitrogen and phosphorus atoms; R$^3$ is selected from the group consisting of hydrogen and lower alkyl radicals; R is selected from the group consisting of hydrocarbyl radicals and hetero atom-substituted derivatives thereof wherein said heteroatoms are selected from the group consisting of halogen, oxygen, sulfur, nitrogen and phosphorus atoms; and v, w x, y and z are integers, except that when x is 0 at least one w is 1; dissolved in a lubricating oil.

2. The composition of claim 1 wherein M is selected from the group consisting of Na, K, Cu, Co, Ni and Fe.

3. The composition of claim 2 wherein R is selected from the group consisting of hydrocarbyl radicals having from about 3 to 1000 carbon atoms.

4. The composition of claim 3 wherein $R^2$ is selected from the group consisting of hydrogen, a lower alkyl-group,

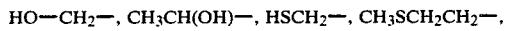
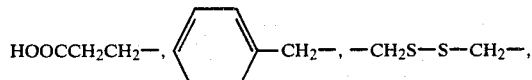
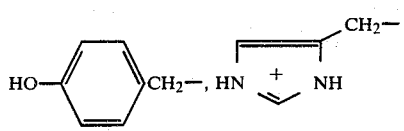
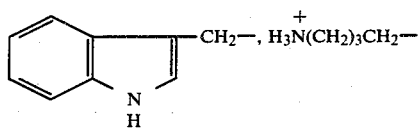
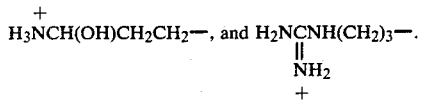

5. The composition of claim 4 wherein $R^2$ is hydrogen.

6. The composition of claim 4 wherein $R^2$ is HOOCCH$_2$—.

7. The composition of claim 5 wherein M is Na and said organometallic additive is present in a sludge-dispersant effective concentration.

8. The composition of claim 5 wherein M is selected from the group consisting of Na, Co and Cu and said organometallic additive is present in an anti-oxidant effective concentration.

9. The composition of claim 5 wherein M is Na and said organometallic additive is present in a rust-inhibiting effective concentration.

10. The composition of claim 5 wherein M is selected from the group consisting of Co, Na and Cu and said organometallic additive is present in an anti-wear effective concentration.

11. The composition of claim 6 wherein M is K and said organometallic additive is present in a rust-inhibiting effective concentration.

12. The composition of claim 6 wherein M is K and said organometallic additive is present in a anti-wear effective concentration.

13. The composition of claim 5 wherein M is Co and said organometallic composition is present in an anti-wear effective concentration.

14. A method for preparing a lubricating oil composition which comprises the steps of:
   (a) reacting formaldehyde with an alpha-amino acid in an aqueous solution comprising a base selected from the group consisting of alkali metal bases;
   (b) reacting the product of step (a) with a phenolic compound to provide an organo compound comprising hydroxyl and alpha-aminocarboxyl groups,
   (c) reacting the product of step (b) with a metal salt comprising a metal ion selected from the group consisting of members of Groups Ib and VIII of the Periodic System of the Elements to provide an oil-soluble organometallic composition comprising said metal ion, and
   (d) dissolving said product of step (c) in a lubricating oil.

15. The method of claim 14 wherein said alpha-amino acid is of the general formula NH$_2$CR$^2$R$^3$COOH wherein $R^2$ is selected from the group consisting of hydrogen, hydrocarbyl radicals and heteroatom-substituted hydrocarbyl radicals wherein said heteroatoms are selected from the group consisting of halogen, oxygen, sulfur, nitrogen and phosphorus atoms; and $R^3$ is selected from the group consisting of hydrogen and lower alkyl radicals.

16. The method of claim 15 wherein said phenolic compound is of the general formula

and R is selected from the group consisting of hydrocarbyl radicals and hetero atom-substituted derivatives thereof wherein said heteroatoms are selected from the group consisting of halogen, oxygen, sulfur, nitrogen and phosphorus atoms.

17. The method of claim 16 further comprising carrying out step (b) in the presence of an alcohol cosolvent.

18. The method of claim 17 wherein said product of step (b) is separated from its reaction mixture as a solid product.

19. The method of claim 18 wherein said solid product is reacted with said metal salt in the presence of a refluxing organic solvent.

20. The method of claim 19 wherein said organic solvent is an ether.

21. A lubricating oil composition prepared according to the method of claim 14.

22. A lubricating oil composition according to claim 21 wherein said metal salt is selected from the group consisting of Cu, Co, Ni and Fe salts.

23. A lubricating oil composition according to claim 22 wherein said alpha-amino acid is of the general formula NH$_2$CR$^2$R$^3$COOH and $R^3$ is a hydrogen radical and $R^2$ is selected from the group consisting of hydrogen and HOOCCH$_2$—.

24. A lubricating oil according to claim 23 wherein $R^2$ is hydrogen and said metal salt is a cobalt salt.

25. A method for preparing a lubricating oil composition which comprises the steps of:
   (a) reacting formaldehyde with an alpha-amino acid in an aqueous solution comprising a base selected from the group consisting of potassium and sodium bases,
   (b) reacting the product of step (a) with a phenolic compound to provide an organo compound comprising hydroxyl and alpha-aminocarboxyl groups, and
   (c) dissolving said product of step (b) in a lubricating oil.

26. The method of claim 25 wherein said base is selected from the group consisting of sodium and potassium hydroxide.

27. The method of claim 26 wherein said alpha-amino acid is of the general formula NH$_2$CR$^2$R$^3$COOH wherein $R^2$ is selected from the group consisting of hydrogen, hydrocarbyl radicals and heteroatom-substituted hydrocarbyl radicals wherein said heteroatoms are selected from the group consisting of halogen, oxygen, sulfur, nitrogen and phosphorus atoms; and $R^3$ is selected from the group consisting of hydrogen and lower alkyl radicals.

28. The method of claim 27 wherein said phenolic compound is of the general formula

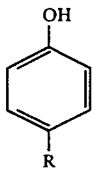

and R is selected from the group consisting of hydrocarbyl radicals and hetero atom-substituted derivatives thereof wherein said heteroatoms are selected from the group consisting of halogen, oxygen, sulfur, nitrogen and phosphorus atoms.

29. The method of claim 28 further comprising carrying out step (b) in the presence of an alcohol cosolvent.

30. The method of claim 29 wherein said product of step (b) is separated from its reaction mixture as a solid product.

31. A lubricating oil composition prepared according to the method of claim 25.

32. A lubricating oil composition prepared according to the method of claim 26.

33. A lubricating oil composition according to claim 32 wherein said alpha-amino acid is of the general formula $NH_2CR^3COOH$ and $R^3$ is a hydrogen radical and $R^2$ is selected from the group consisting of hydrogen and $HOOCCH_2-$.

34. A lubricating oil according to claim 33 wherein $R^2$ is hydrogen and said base is sodium hydroxide.

35. A lubricating oil according to claim 24 wherein $R^2$ is $HOOCCH_2-$ and said base is potassium hydroxide.

* * * * *